US012390620B2

United States Patent
Beeckler et al.

(10) Patent No.: US 12,390,620 B2
(45) Date of Patent: Aug. 19, 2025

(54) CONTACT FORCE SPRING WITH MECHANICAL STOPS

(71) Applicant: Biosense Webster (Israel) Ltd., Yokneam (IL)

(72) Inventors: Christopher Thomas Beeckler, Brea, CA (US); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 975 days.

(21) Appl. No.: 16/726,605

(22) Filed: Dec. 24, 2019

(65) Prior Publication Data

US 2021/0187254 A1 Jun. 24, 2021

(51) Int. Cl.
*A61M 25/10* (2013.01)
*A61B 5/00* (2006.01)
*A61B 18/14* (2006.01)
*A61M 39/10* (2006.01)
(Continued)

(52) U.S. Cl.
CPC ........... *A61M 25/10* (2013.01); *A61B 5/6853* (2013.01); *A61B 18/1482* (2013.01); *A61B 18/1492* (2013.01); *A61M 39/10* (2013.01); *A61B 5/6885* (2013.01); *A61B 2018/00172* (2013.01); *A61B 2018/0022* (2013.01); *A61B 2018/00577* (2013.01); *A61M 2025/0059* (2013.01); *A61M 2039/1033* (2013.01); *A61M 2205/332* (2013.01)

(58) Field of Classification Search
CPC .................. A61M 25/10; A61M 39/10; A61M 2025/0059; A61M 2205/332; A61M 2039/1033; A61B 5/6853; A61B 5/6885; A61B 18/1482; A61B 18/1492; A61B 2018/00172; A61B 2018/0022; A61B 2018/00577
See application file for complete search history.

(56) References Cited

U.S. PATENT DOCUMENTS

| 6,623,480 B1 * | 9/2003 | Kuo ................... A61B 18/1492 606/41 |
| 9,101,734 B2 * | 8/2015 | Selkee .............. A61M 25/0147 |

(Continued)

FOREIGN PATENT DOCUMENTS

| EP | 3189806 A1 | 7/2017 |
| JP | 2013192947 A | 9/2013 |
| JP | 2018143771 A | 9/2018 |

OTHER PUBLICATIONS

Active Spring Components http://www.dent-wiki.com/dental_technology/active-spring-components.
(Continued)

*Primary Examiner* — Michael F Peffley
*Assistant Examiner* — Bo Ouyang (57) ABSTRACT

A catheter apparatus, including an elongated deflectable element, a distal assembly, a force sensor disposed between the elongated deflectable element and the distal assembly, and comprising a spring including a tube with at least one helical cut extending around a circumference of the tube, the at least one helical cut including deviations extending in a longitudinal direction of the tube, the deviations being configured to prevent overstretching and overbending of the spring.

19 Claims, 10 Drawing Sheets

(51) Int. Cl.
*A61B 18/00* (2006.01)
*A61M 25/00* (2006.01)

(56) References Cited

U.S. PATENT DOCUMENTS

| | | | | |
|---|---|---|---|---|
| 2008/0294158 | A1* | 11/2008 | Pappone | A61B 18/1492 |
| | | | | 606/41 |
| 2011/0130648 | A1 | 6/2011 | Beeckler et al. | |
| 2011/0263934 | A1 | 10/2011 | Aeby et al. | |
| 2012/0253167 | A1* | 10/2012 | Bonyak | A61B 5/062 |
| | | | | 600/409 |
| 2013/0253503 | A1* | 9/2013 | Govari | A61B 18/1492 |
| | | | | 606/41 |
| 2014/0005661 | A1* | 1/2014 | Shelton, IV | A61B 34/37 |
| | | | | 606/41 |
| 2016/0339207 | A1 | 11/2016 | Beeckler et al. | |
| 2017/0319269 | A1* | 11/2017 | Oliverius | A61M 39/12 |
| 2018/0256247 | A1 | 9/2018 | Govari et al. | |
| 2018/0271590 | A1* | 9/2018 | Basu | A61M 25/0043 |
| 2018/0338811 | A1 | 11/2018 | Miklos et al. | |
| 2019/0247622 | A1* | 8/2019 | Romano | A61M 25/09 |

OTHER PUBLICATIONS

A (Near) Real-Time Simulation Method of Aneurysm Coil Embolization; ResearchGate; Book: Aug. 2012; http://www.researchgate.net/publication/278763087; pp. 232-233.
Extended European Search Report dated May 11, 2021, from corresponding European Application No. 20217038.7.
Examination Report dated May 28, 2024, from corresponding European Application No. 20217038.7.
Search Report dated Jun. 28, 2024, from corresponding Japanese Application No. 2020-213426.
English translation of Notice of Reasons for Refusal dated Jul. 9, 2024, from corresponding Japanese Application No. 2020-213426.

* cited by examiner

CONTACT FORCE SPRING WITH MECHANICAL STOPS

FIELD OF THE INVENTION

The present invention relates to medical equipment, and in particular, but not exclusively to, contact force springs.

BACKGROUND

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

US Patent Publication 2011/0263934 of Aeby, et al., describes a catheter for diagnosis or treatment of a vessel or organ is provided in which a flexible elongated body includes a tri-axial force sensor formed of a housing and a plurality of optical fibers associated with the housing that measure changes in the intensity of light reflected from the lateral surfaces of the housing resulting from deformation caused by forces applied to a distal extremity of the housing. A controller receives an output of the optical fibers and computes a multi-dimensional force vector corresponding to the contact force.

US Patent Publication 2011/0130648 of Beeckler, et al., describes a medical probe, consisting of a flexible insertion tube, having a distal end for insertion into a body cavity of a patient, and a distal tip, which is disposed at the distal end of the flexible insertion tube is configured to be brought into contact with tissue in the body cavity. The probe also includes a coupling member, which couples the distal tip to the distal end of the insertion tube and which consists of a tubular piece of an elastic material having a plurality of intertwined helical cuts therethrough along a portion of a length of the piece.

US Patent Publication 2016/0339207 of Beeckler, et al., describes a catheter having a catheter shaft that has a more uniform construction throughout its length and is able to provide more than one deflection curvature. The catheter shaft includes a flexible outer tubular member, and a less flexible inner tubular member extending through the outer tubular member in a proximal section of the catheter shaft, wherein the inner tubular member is afforded longitudinal movement relative to the outer tubular member. The catheter also includes at least one puller wire extending through the inner tubular member to deflect a distal deflection section of the catheter shaft, wherein longitudinal movement of the inner tubular member relative to the outer tubular member enables an operator to select and set a deflection curvature of the distal deflection section.

SUMMARY

There is provided in accordance with an embodiment of the present disclosure, a catheter apparatus, including an elongated deflectable element, a distal assembly, a force sensor disposed between the elongated deflectable element and the distal assembly, and including a spring including a tube with at least one helical cut extending around a circumference of the tube, the at least one helical cut including deviations extending in a longitudinal direction of the tube, the deviations being configured to prevent overstretching and overbending of the spring.

Further in accordance with an embodiment of the present disclosure respective ones of the deviations include respective opposing sigmoid curves.

Still further in accordance with an embodiment of the present disclosure respective ones of the deviations of the helical cuts define respective mechanical stops, each mechanical stop including opposing surfaces which are configured to come into contact with each other to prevent overstretching and overbending of the spring.

Additionally, in accordance with an embodiment of the present disclosure respective ones of the mechanical stops are configured to engage simultaneously so that a force applied on the spring is shared among the respective mechanical stops to prevent sequential failure of the respective mechanical stops.

Moreover, in accordance with an embodiment of the present disclosure the at least one helical cut includes multiple helical cuts, respective ones of the mechanical stops of each of the helical cuts being configured to engage simultaneously.

Further in accordance with an embodiment of the present disclosure the at least one helical cut includes multiple helical cuts, the mechanical stops of each of the helical cuts being configured to engage simultaneously.

Still further in accordance with an embodiment of the present disclosure respective ones of the mechanical stops include respective T-shape elements disposed in respective T-shape openings.

Additionally, in accordance with an embodiment of the present disclosure respective ones of the mechanical stops include respective L-shape elements disposed in respective L-shape openings.

Moreover, in accordance with an embodiment of the present disclosure respective ones of the mechanical stops include respective loops and sockets.

Further in accordance with an embodiment of the present disclosure the at least one helical cut includes multiple helical cuts, the tube including three of the helical cuts.

Still further in accordance with an embodiment of the present disclosure, the apparatus includes a proximal coupler having a proximal and distal end, wherein the elongated deflectable element has a distal end connected to the proximal end of the proximal coupler, the tube and the distal end of the proximal coupler including complementary bayonet connecting features connecting the distal end of the proximal coupler with the tube.

Additionally, in accordance with an embodiment of the present disclosure, the apparatus includes a distal coupler, wherein the tube has a distal end including holes disposed around the circumference of the tube, the distal end of the tube being connected to the distal coupler via an adhesive which extends into respective ones of the holes.

Moreover, in accordance with an embodiment of the present disclosure the tube includes a distal edge with openings therein, the distal coupler including protrusions configured for engaging the openings to prevent rotation of the distal coupler with respect to the tube.

Further in accordance with an embodiment of the present disclosure the openings include U-shaped openings.

Still further in accordance with an embodiment of the present disclosure, the apparatus includes a distal coupler, wherein the tube includes a distal edge with openings therein, the distal coupler including protrusions configured for engaging the openings to prevent rotation of the distal coupler with respect to the tube.

Additionally, in accordance with an embodiment of the present disclosure the openings include U-shaped openings.

Moreover, in accordance with an embodiment of the present disclosure the distal assembly includes an expandable distal assembly.

Further in accordance with an embodiment of the present disclosure the expandable distal assembly includes an inflatable balloon.

Still further in accordance with an embodiment of the present disclosure the force sensor includes a transmitting coil and at least one receiving coil disposed on the tube.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

An assembly, such as a balloon, at the tip of a contact force sensor of a catheter presents a unique challenge to a contact force spring of the force sensor. The spring experiences significantly higher tensile forces as the assembly is withdrawn into the catheter sheath, or other such maneuvers. In addition to the withdrawal forces, even during normal use side and other forces exerted on the spring are higher than those exerted with a focal catheter due to the length of the assembly, e.g., a balloon.

For example, the contact force spring may be formed from one or more helices cut around a tube. The spring functions very well when attached to a focal catheter. However, in the case of other catheters such as a balloon catheter, the higher forces on the spring, typically when the balloon is withdrawn into its sheath, or pulling the balloon on a Haemostatic valve, can permanently damage the spring, for example, the ends of the helical cuts may open too much.

Embodiments of the present invention solve the above problems by adding deviations in the helical cut(s) in a spring to provide mechanical stops which prevent overbending and overstretching of the spring. The mechanical stops are designed to engage once the spring has been extended by a preset amount, and the engagement prevents plastic deformation, which is irreversible, of the spring. The mechanical stops are generally designed to prevent overstretching while still allowing for compression of the spring so that the spring can still perform its main function in measuring force. Alternate shapes of mechanical stops are possible.

In some embodiments, the mechanical stops are designed to engage simultaneously rather than sequentially in order to share the load evenly, otherwise one (or more) mechanical stop(s) will take the entire load until it (or they) fails, at which point the next mechanical stop(s) would take the load, etc.

In some embodiments, a catheter includes an elongated deflectable element, a distal assembly (which may include an expandable distal assembly, e.g., including an inflatable balloon), a force sensor disposed between the elongated deflectable element and the distal assembly. The force sensor includes a tube with helical cuts extending around a circumference of the tube. Each helical cut includes deviations extending in a longitudinal direction of the tube. The deviations prevent overstretching and overbending of the spring. The force sensor may include position coils disposed on the tube.

The tube may include any suitable number of helical cuts, for example, two, three, or more than three. The term "helical cut", as used in the specification and claims, is defined as a helical cut extending more than one turn around the tube, or extending at least half of a turn around the tube.

Respective deviations of respective helical cuts define respective mechanical stops. Each mechanical stop includes opposing surfaces which come into contact with each other to prevent overstretching and overbending of the spring.

In some embodiments, respective mechanical stops are designed to engage simultaneously so that a force applied on the spring is shared among the respective mechanical stops to prevent sequential failure of the respective mechanical stops. In some embodiments, at least two mechanical stops of each helical cut are designed to engage simultaneously. In some embodiments, all the mechanical stops of each helical cut are designed to engage simultaneously.

In some embodiment the deviations include respective opposing sigmoid curves. In some embodiments, respective mechanical stops include respective loops and sockets. In some embodiments, respective mechanical stops include respective T-shape elements placed in respective T-shape openings. In some embodiment, respective mechanical stops include respective L-shape elements placed in respective L-shape openings.

In some embodiments, the catheter includes a proximal coupler having a proximal end connected to the distal end of the elongated deflectable element. The tube and the distal end of the proximal coupler include complementary bayonet connecting features connecting the distal end of the proximal coupler with the tube.

In some embodiments, the catheter includes a distal coupler and the distal end of the tube includes holes around its circumference. The distal end of the tube is connected to the distal coupler via an adhesive (such as epoxy) which extends into the holes to promote adhesion between the distal coupler and the tube.

In some embodiments, the distal edge of the tube includes openings (e.g., U-shape openings) for engaging protrusions of the distal coupler to prevent rotation of the distal coupler with respect to the tube.

System Description

Figure 1:
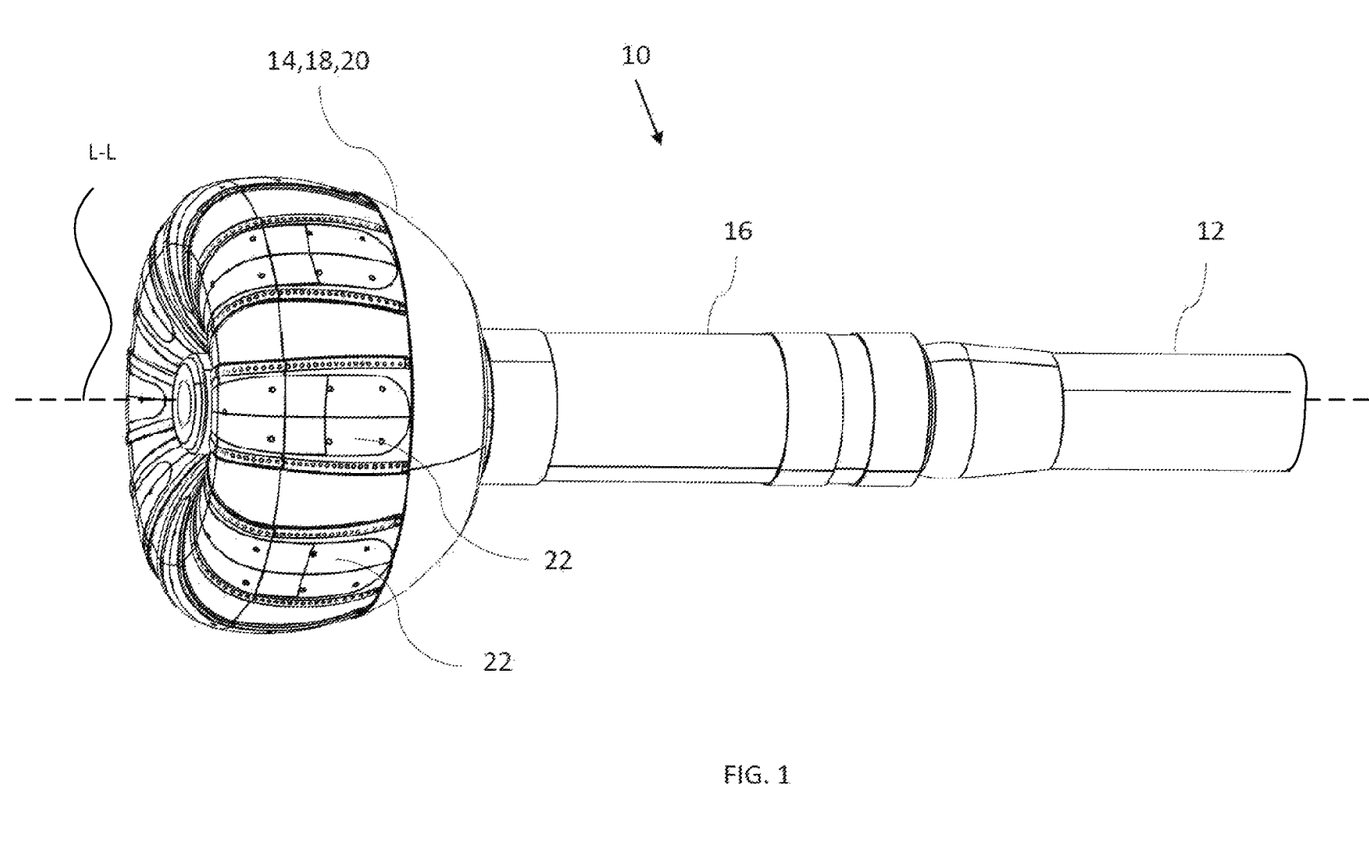
FIG. 1 is a schematic view of a catheter constructed and operative in accordance with an embodiment of the present invention.

Reference is now made to FIG. 1, which is a schematic view of a catheter 10 constructed and operative in accordance with an embodiment of the present invention. The catheter 10 includes an elongated deflectable element 12, a distal assembly 14 and an outer sleeve 16 disposed about a longitudinal axis L-L (which will be used to reference various internal and external components of catheter 10). The distal assembly 14 may include any suitable distal assembly, for example, a lasso catheter assembly or a focal catheter assembly. In some embodiments, the distal assembly 14 includes an expandable distal assembly 18, which may include an inflatable balloon 20 or a basket, by way of example only. The elongated deflectable element 12 includes lumens (not shown) in which to carry electrical connections, irrigation channels, puller wires, and the like. The distal assembly 14 may also include multiple electrodes 22 (only two labeled for the sake of simplicity) disposed thereon for use in mapping and/or ablation or any other suitable function.

Figure 2A:
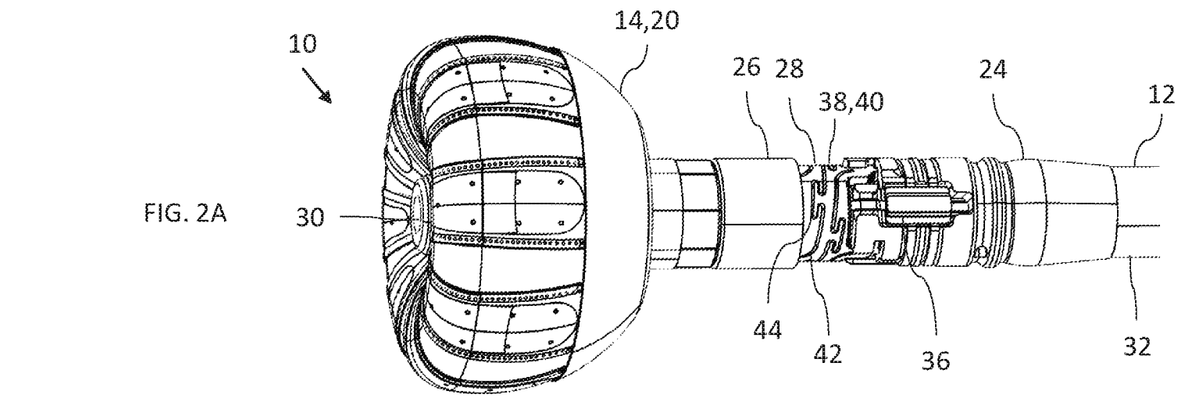
FIGS. 2A-B are schematic views of the catheter of FIG. 1 with an outer sleeve removed.
Figure 2B:
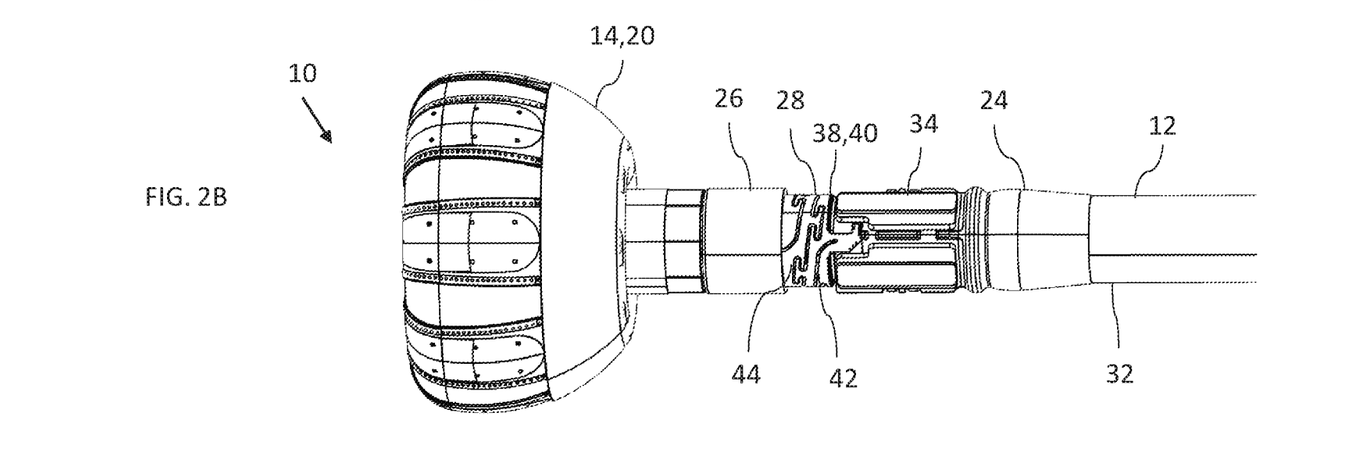

Reference is now made to FIGS. 2A-B, which are schematic views of different sides of the catheter 10 of FIG. 1 with the outer sleeve 16 of FIG. 1 removed. The catheter 10 includes a proximal coupler 24, a distal coupler 26, and a force sensor 28.

The force sensor 28 is disposed between the elongated deflectable element 12 and the distal assembly 14, and more specifically disposed between the proximal coupler 24 and the distal coupler 26.

The force sensor 28 includes a spring 38 including a tube 40 with one or more helical cuts 42 extending around a circumference of the tube 40. As used herein, the circumference includes both the outer circumferential surface 41A and the inner circumferential surface 41B of the tubular member 40. Each helical cut 42 includes deviations 44 extending in a longitudinal direction of the tube 40. The deviations 44 are configured to prevent overstretching and overbending of the spring 38. The spring 38 is described in more detail with reference to FIGS. 7A-8C.

The inflatable balloon 20 is mounted on the distal coupler 26 with the distal coupler 26 extending until a nose 30 in the center of the distal end of the inflatable balloon 20. Therefore, the distal coupler 26 couples the inflatable balloon 20 with the force sensor 28. The distal coupler 26 is described in more detail with reference to FIGS. 4, 6A-B.

The proximal coupler 24 couples the force sensor 28 with a distal end 32 of the elongated deflectable element 12. The catheter 10 includes a position sensor 34 (FIG. 2B), such as a single, dual, and/or triple-axis coil. The position sensor 34 is mounted on the proximal coupler 24 in the examples of FIG. 2B. The catheter 10 also includes a solder pad 36 (FIG. 2A) disposed on the proximal coupler 24 to which various electrical connections from components at the distal end of the catheter 10 and electrical connections from the proximal end of the catheter 10 may be connected. The proximal coupler 24 is described in more detail with reference to FIGS. 5A-C.

Figure 3:
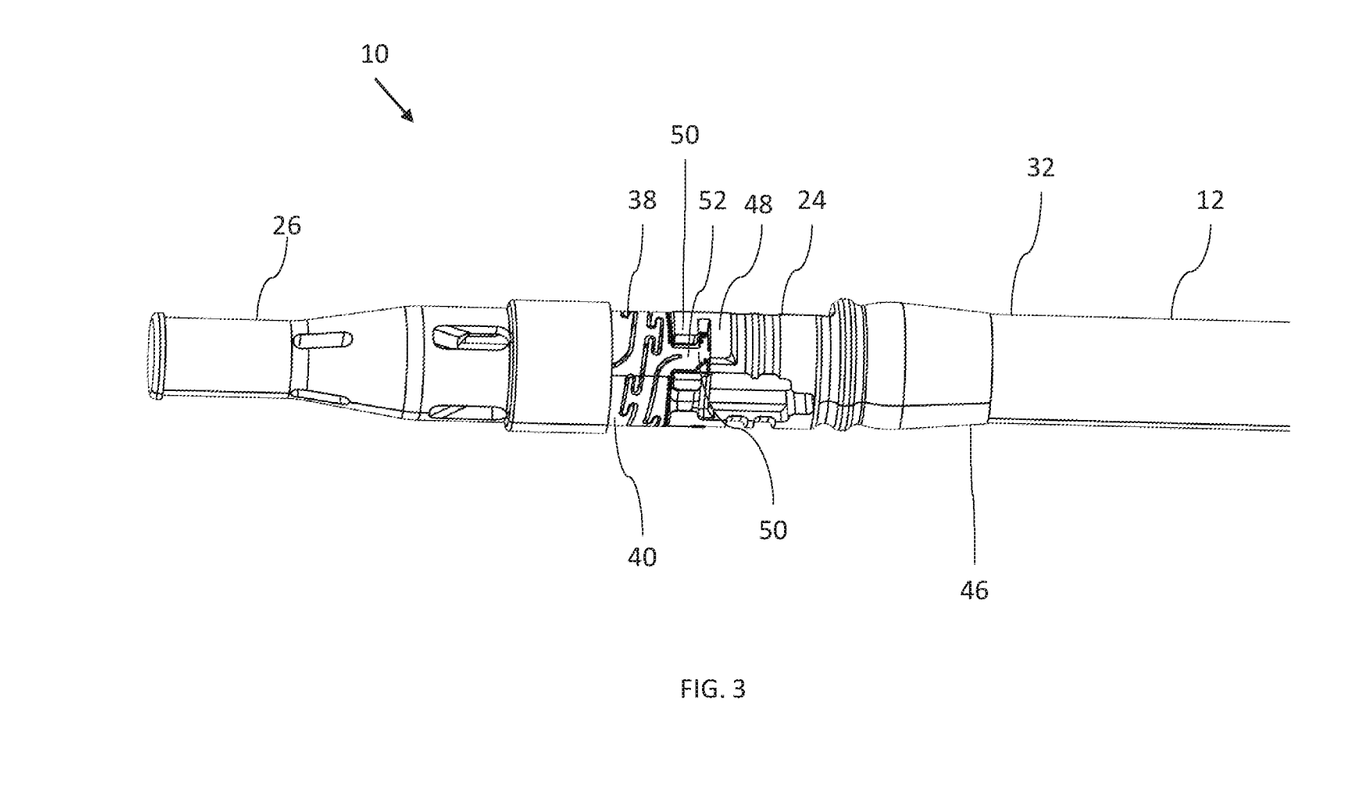
FIG. 3 is a schematic view of the catheter of FIG. 1 with several elements removed.
Figure 4:
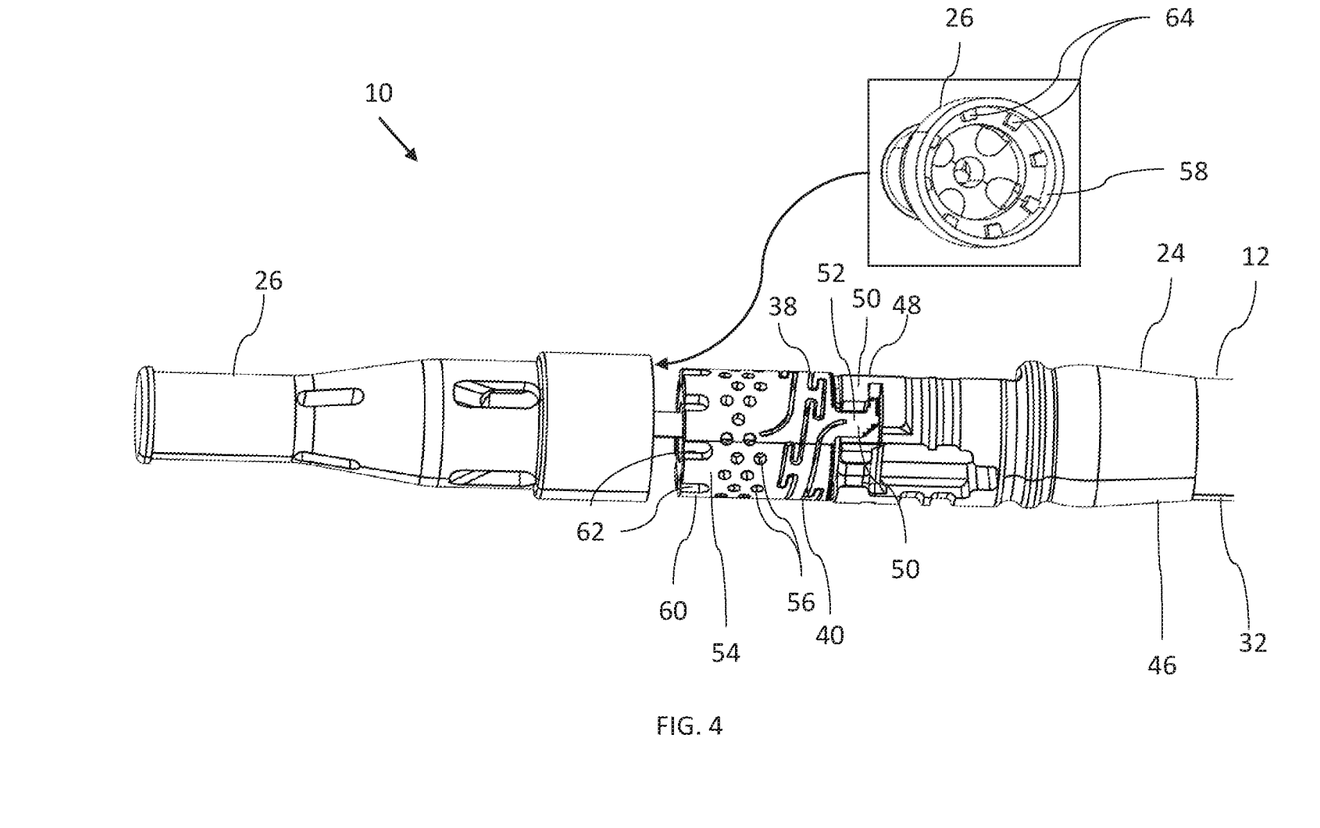
FIG. 4 is a partially exploded view of the catheter as shown in FIG. 3.

Reference is now made to FIGS. 3 and 4. FIG. 3 is a schematic view of the catheter 10 of FIG. 1 with several elements removed. FIG. 3 shows the catheter 10 with the distal assembly 14 and the sleeve 16 of FIG. 1 removed, and with the solder pad 36 and the position sensor 34 of FIGS. 2A and 2B removed. FIG. 4 is a partially exploded view of the catheter 10 as shown in FIG. 3. FIG. 4 shows the distal coupler 26 pulled away from the spring 38 to show how the distal coupler 26 and the spring 38 are connected to each other.

The distal end 32 of the elongated deflectable element 12 is connected to a proximal end 46 of the proximal coupler 24. A proximal end 52 of the tube 40 and a distal end 48 of the proximal coupler 24 include complementary bayonet connecting features 50 connecting the distal end 48 of the proximal coupler with the proximal end 52 of the tube 40. The bayonet connecting features 50 are described in more detail with reference to FIGS. 5A-C and FIGS. 7A-B.

FIG. 4 shows that a distal end 54 of the tube 40 comprises holes 56 (only some labeled for the sake of simplicity) disposed around the circumference of the tube 40. The distal end 54 of the tube 40 is connected to the distal coupler 26 distal coupler via an adhesive, e.g., epoxy, which extends into respective ones of the holes 56 thereby improving a bond between the distal end 54 of the tube 40 and an inner proximal surface 58 of the distal coupler 26. The holes 56 are described in more detail with reference to FIGS. 7A-B.

A distal edge 60 of the tube 40 includes openings 62 (only some labeled for the sake of simplicity) disposed around the circumference of the distal edge 60. The inner proximal surface 58 of the distal coupler 26 includes protrusions 64 (only some labeled for the sake of simplicity), disposed circumferentially around the inner proximal surface 58, and configured for engaging the openings 62 (or slots disposed around the perimeter of the generally tubular member 38) to prevent rotation of the distal coupler 26 with respect to the tube 40. The openings 62 and the protrusions 64 may be any suitable shape. In some embodiments, the openings 62 include U-shaped openings as shown in the example of FIG. 4 or rectangular shape openings. The openings 62 and the protrusions 64 are described in more detail with reference to FIG. 6B and FIGS. 7A-B.

Figure 5A:
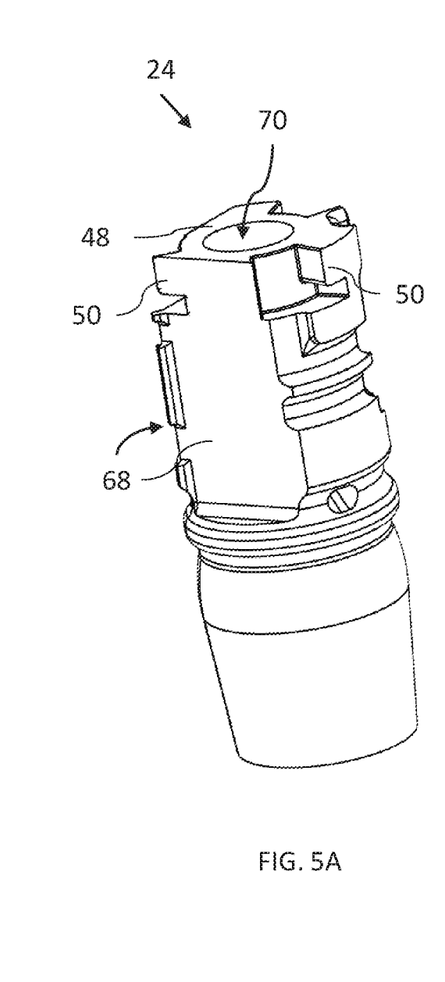
FIGS. 5A-C are schematic views of a proximal coupler of the catheter of FIG. 1.
Figure 5B:
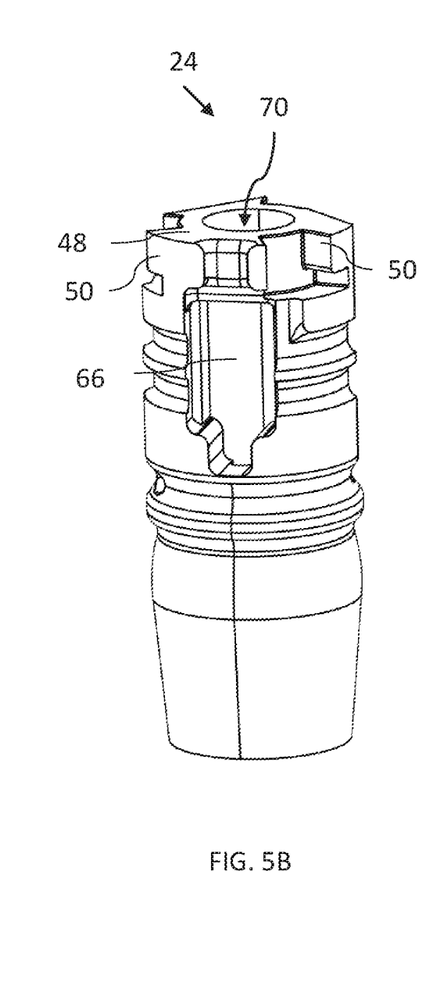
Figure 5C:
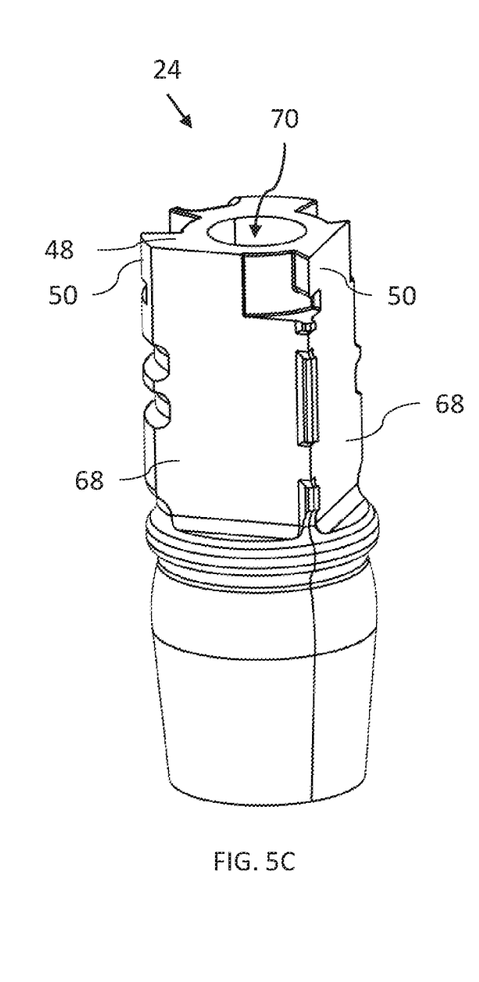

Reference is now made to FIGS. 5A-C, which are schematic views of various sides of the proximal coupler 24 of the catheter 10 of FIG. 1. The proximal coupler 24 has a generally cylindrical shape with a central lumen 70 for passing various elements therein such as wires and an irrigation tube (not shown). The distal end 48 includes the bayonet connecting features 50 which may have any suitable shape, for example, but not limited to an L-shape recess. In some embodiments the distal end 48 includes three bayonet connecting features 50. However, the distal end 48 may include more or less than three bayonet connecting features 50. The proximal coupler 24 includes a recess 66 (FIG. 5B) for accepting the solder pad 36 (FIG. 2A) therein in addition to allowing a passage for wires connected to solder pad 36 to pass into coupler 24. Coupler 24 also includes two flat surfaces 68 (FIGS. 5A and 5C) for accepting the position sensor 34 (FIG. 2B) thereon. The proximal coupler 24 may be formed from any suitable material or combination of materials, for example, but not limited to, polycarbonate with or without glass filler, polyether ether ketone (PEEK) with or without glass filler, or polyetherimide (PEI) with or without glass filler. The proximal coupler 24 may have any suitable outer diameter, for example, in a range of 1 mm to 10 mm.

Figure 6A:
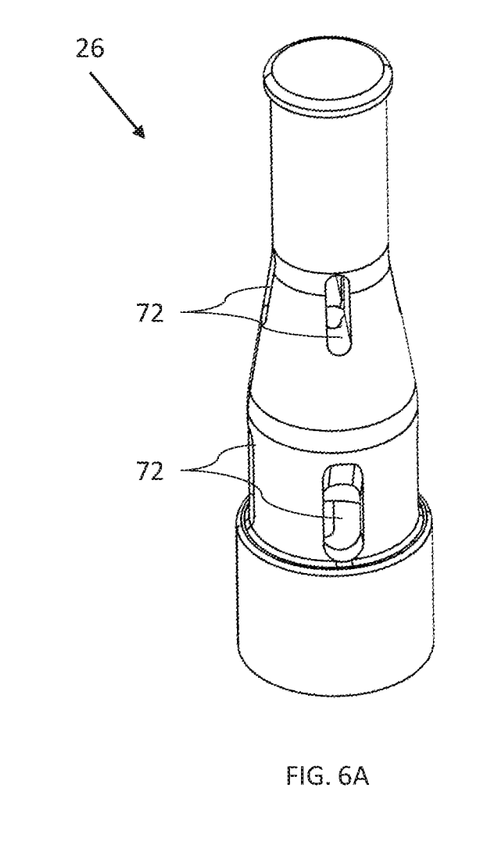
FIGS. 6A-B are schematic views of the distal coupler of the catheter of FIG. 1.
Figure 6B:
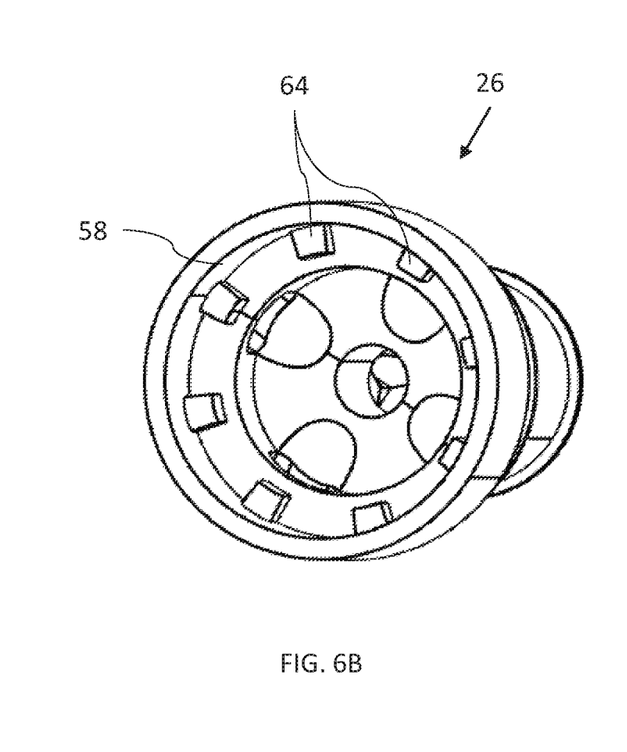

Reference is now made to FIGS. 6A-B, which are schematic views of the distal coupler 26 of the catheter 10 of FIG. 1. FIG. 6A shows that the distal coupler 26 includes openings 72 for irrigation and/or feeding wires to the electrodes 22 (FIG. 1) of the distal assembly 14 (FIG. 1). In some embodiments, the openings 72 may be disposed around a circumference of the distal coupler 26 in a proximal portion of the distal coupler 26 and/or in a distal portion of the distal coupler 26. The distal coupler 26 may include any suitable number of openings 72, for example, in a range between 1 and 12 openings 72, such as 8 openings.

FIG. 6B shows the inner proximal surface 58 and its protrusions 64 (only some labeled for the sake of simplicity). The distal coupler 26 may include any suitable number of protrusions 64 to engage with the openings 62 (FIG. 4) of the tube 40 (FIG. 4). In some embodiments, the distal coupler 26 includes eight protrusions 64, but may be in the range of 1 to 30 protrusions 64, by way of example. The protrusions 64 may have any suitable dimensions, in the order of 0.05 mm to 10 mm and may depend on the number of protrusions 64. The distal coupler 26 may be formed from any suitable material or combination of materials, for example, but not limited to, polycarbonate with or without glass filler, polyether ether ketone (PEEK) with or without glass filler, or polyetherimide (PEI) with or without glass filler. The distal coupler 26 may have any suitable outer diameter, for example, in a range of 1 mm to 10 mm.

Figure 7A:
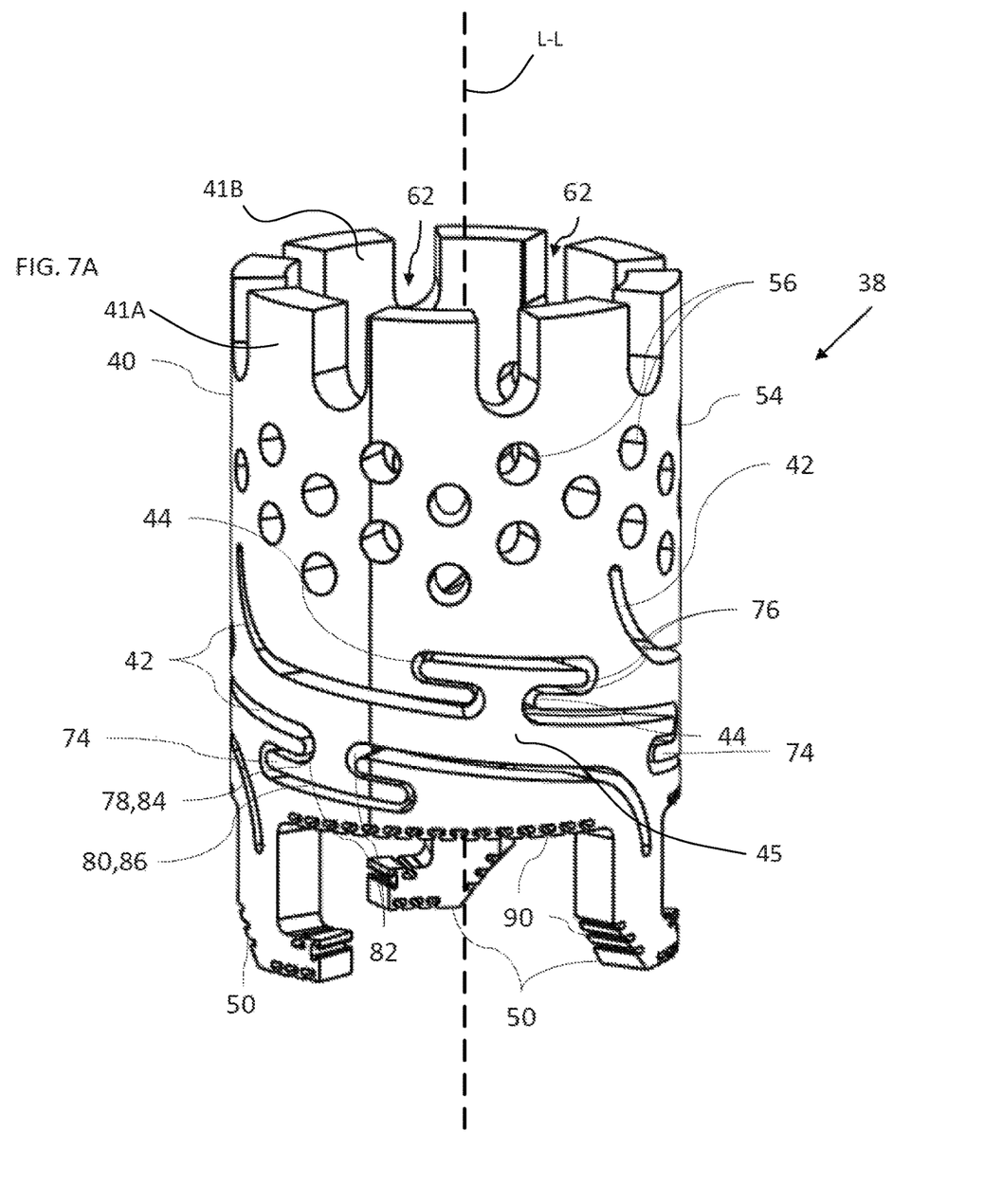
FIGS. 7A-B are schematic views of a spring of the catheter of FIG. 1.
Figure 7B:
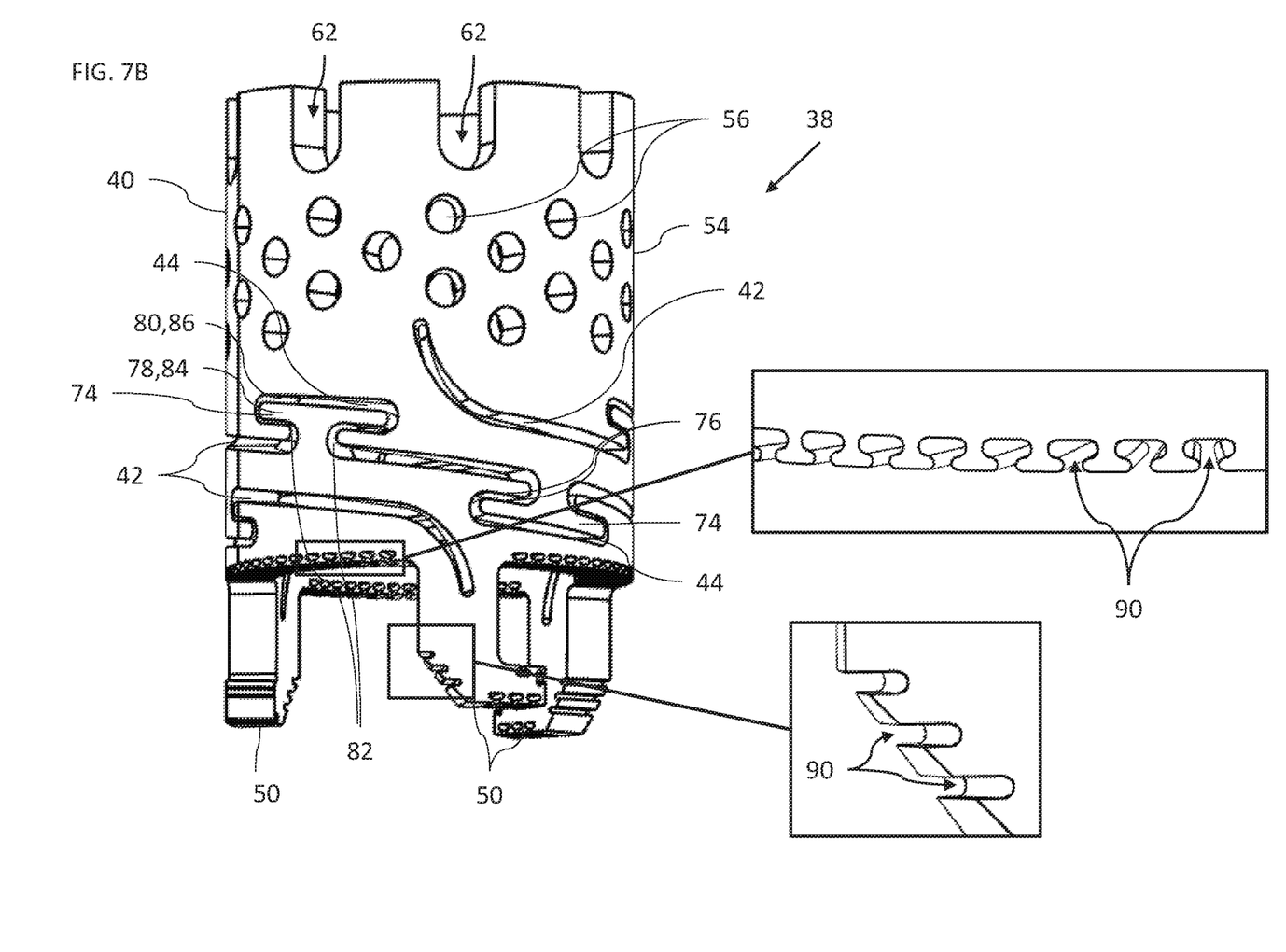

Reference is now made to FIGS. 7A-B, which are schematic views of the spring 38 of the catheter 10 of FIG. 1. As previously mentioned, the spring 38 includes the tube 40 with helical cuts 42 extending around a circumference of the tube 40. As seen in FIG. 7A, two generally parallel helical cuts extend through the tubular member 38 while traversing along the longitudinal axis L-L to define a helical shaped spring member 45 (between the gaps 42) which is separated from the tubular member 38 by the gaps or cuts 42. As shown in FIG. 7A, three helical spring members 45 are provided. The helical cuts 42 provide the coupler 38 with its ability to bend and compress while provide a resistance to bending and compression. Each helical cut 42 includes deviations 44 extending in a longitudinal direction (approximately parallel to the axis L-L) of the tube 40. The deviations 44 are configured to prevent overstretching and overbending of the spring 45 by having a portion of the spring 45 configured to interlock with another portion of the tubular member 38 via a suitable interlock 44.

The helical cuts 42 extend from the outer surface of the tube 40 through to the inner surface of the tube 40. The helical cuts 42 may be right-handed helices or left-handed helices. The pitch of each helical cut 42 may be any suitable value, for example in the range of 0.2 mm to 5 mm. The helical cuts 42 may have any suitable width, for example, in the range of 0.05 mm to 0.5 mm, such as 0.1 mm. The spring 38 may include any suitable number of helical cuts 42, for example, two helical cuts 42 forming a double helix, or three helical cuts 42 forming a triple helix, and so on. The helical cuts 42 are generally circular helices disposed about a longitudinal axis L-L extending through the center of member 38. Each of the helical cuts 42 may extend around the circumference for any suitable amount of turns, including extending for less than one turn but at least half a turn. For example, any of the helical cuts 42 may extend 1.5 turns, 1 turn, two-thirds of a turn (as shown in FIGS. 7A and 7B), or half a turn. In the example of FIGS. 7A-B, respective ones of the helical cuts 42 extend from respective ones of the bayonet connecting features 50 up and around the circumference of the tube 40.

Respective ones of the deviations 44 of respective ones of the helical cuts 42 define respective mechanical stops 74 (only some labeled for the sake of simplicity). Each mechanical stop 74 includes opposing surfaces 76 (only some labeled for the sake of simplicity) which are configured to come into contact with each other to prevent overstretching and overbending of the spring 38. In some embodiments, the opposing surfaces 76 of respective ones of the mechanical stops 74 are configured to engage simultaneously so that a force applied on the spring 38 is shared among the respective mechanical stops 74 to prevent sequential failure of the respective mechanical stops 74. In some embodiments, at least two, and generally all, of the mechanical stops 74 of each helical cut 42 are configured to engage simultaneously. In some embodiments, respective ones of the mechanical stops 74 include respective loops 78 and sockets 80 (only one labeled for the sake of simplicity).

In some embodiments, respective one of the deviations 44 include respective opposing sigmoid curves 82 (only two labeled for the sake of simplicity) with characteristic S-shapes so that the deviations 44, and the mechanical stops 74, are formed by an S-shape and a reversed S-shape as shown in FIGS. 7A-B. In some embodiments, respective ones of the mechanical stops 74 include respective T-shape elements 84 disposed in respective T-shape openings 86.

The bayonet connecting features 50 of the tube 40 are generally L-shaped and are configured to connect with the bayonet connecting features 50 of the proximal coupler 24 (FIGS. 5A-C). The tube 40 may include any suitable number of bayonet connecting features 50, for example, one, two, three or more.

The holes 56 (only some labeled for the sake of simplicity) in the distal end 54 of the tube 40 are disposed around the circumference of the tube 40. The tube 40 may include any suitable number of holes 56, for example, two or more. The maximum number of holes 56 is generally restricted by the available space on the tube 40 above the helical cuts 42. Each hole 56 may have any suitable diameter, for example, in the range of 0.05 mm to 0.5 mm.

In some embodiments, the tube 40 includes eight openings 62 (only some labeled for the sake of simplicity), but may have any suitable number of openings 62, for example, in the range of 1 to 30 openings 62. The openings 62 may have any suitable dimensions, in the order of 0.05 mm to 10 mm and may depend on the number of openings 62.

The lower surface of the tube 40 may include notches 90 (only some labeled for the sake of simplicity) to enhance adhesive connection between the lower surface of the tube 40 and other elements of the catheter 10, such as proximal coupler 24.

The helical cuts 42, holes 56, and openings 62 may be formed by any suitable method, for example, by laser machining, electric discharge machining, or conventional machining. The tube 40 may have any suitable outer diameter, for example, in the range of 1 mm to 10 mm. The tube 40 may have any suitable wall thickness, for example, in the range of 0.1 mm to 3 mm. The tube may be formed from any suitable material, for example, Nitinol, beta titanium, beryllium copper, or phosphor bronze.

Figure 8A:
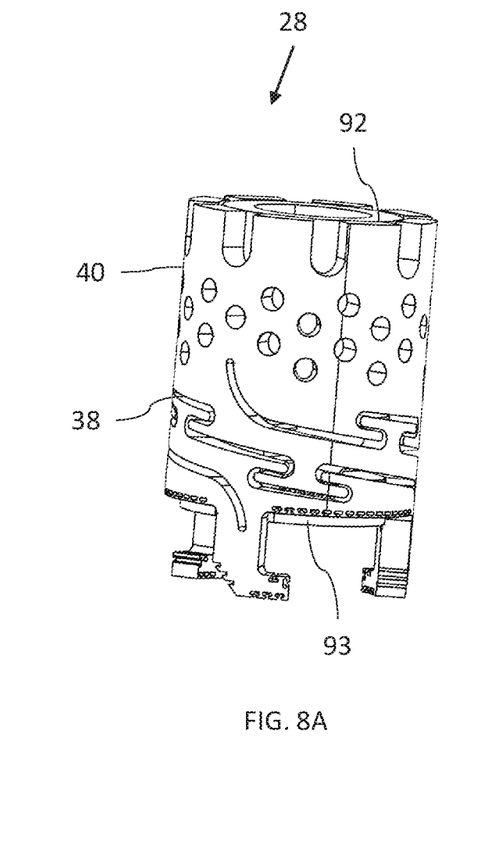
FIGS. 8A-C are schematic views of a force sensor of the catheter of FIG. 1.
Figure 8B:
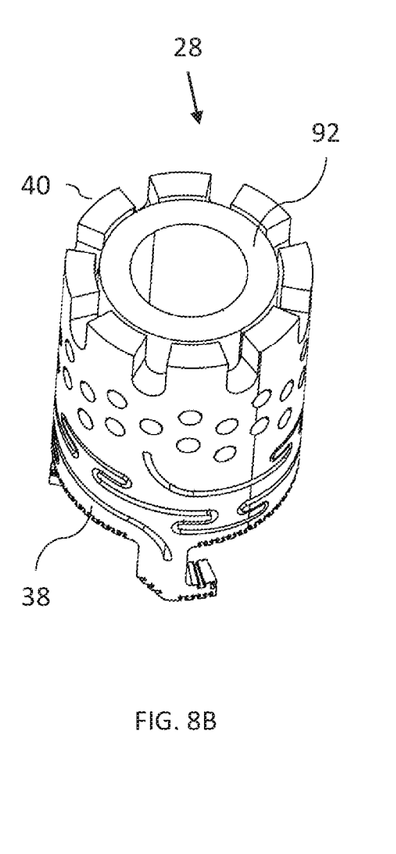
Figure 8C:
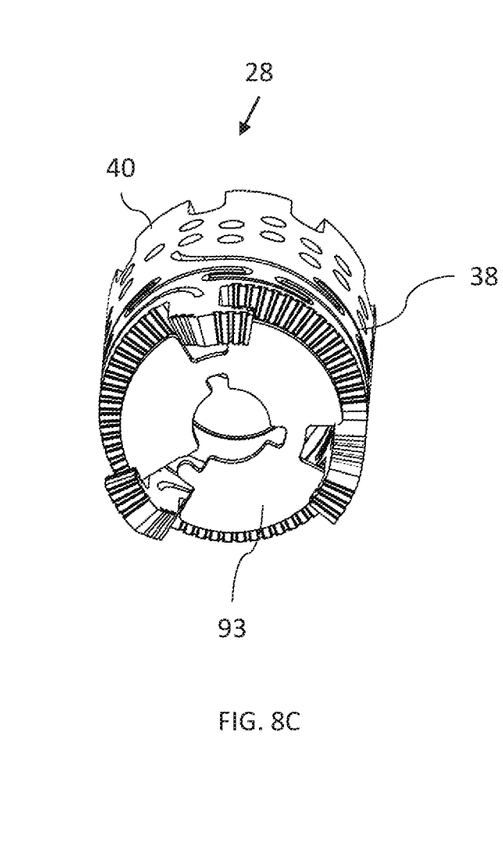

Reference is now made to FIGS. 8A-C, which are schematic views of the force sensor 28 of the catheter 10 of FIG. 1. The force sensor 28 includes the spring 38 and a transmitting coil 92 disposed on the top and receiving coils 93 disposed on the bottom of the tube 40. The receiving coils 93 receive a transmitted signal from the transmitting coil 92. The received signal is representative of a distance between the transmitting coil 92 and the receiving coils 93 thereby providing an indication of a force applied to the force sensor 28. Any suitable transmitting coil 92, and receiving coils 93 may be used, for example, the coils described in US Patent Publication 2018/0256247 of Govari, et al. which is incorporated by reference with a copy provided in the Appendix. In some embodiments, the positioning of the transmitting coil 92 and the receiving coils 93 may be reversed or in any suitable position. In some embodiments, the force sensor 28 may include a single receiving coil and multiple transmitting coils, or any suitable combination thereof.

Figure 9:
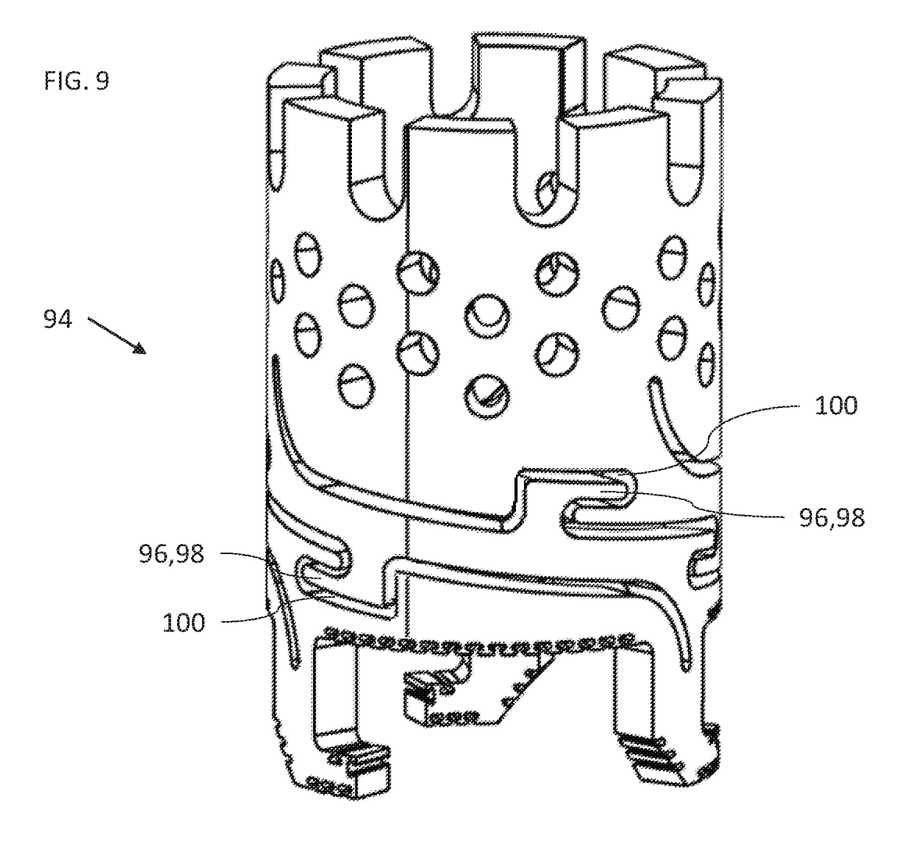
FIG. 9 is a schematic view of a spring constructed and operative in accordance with an alternative embodiment of the present invention.

Reference is now made to FIG. 9, which is a schematic view of a spring 94 constructed and operative in accordance with an alternative embodiment of the present invention. The spring 94 includes mechanical stops 96. Respective mechanical stops 96 include respective L-shape elements 98 disposed in respective L-shape openings 100.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A catheter apparatus, comprising:
an elongated deflectable element;
a distal assembly;
a force sensor disposed between the elongated deflectable element and the distal assembly, and comprising a spring including a tube with at least one helical cut defining a helical path extending less than one full turn around a circumference of the tube and defining at least a portion of a helical-shaped spring member, the helical-shaped spring member comprising a proximal side positioned on a first side of the helical path and having a first mechanical stop and a distal side positioned on a second side of the helical path and having a second mechanical stop arranged immediately following the first mechanical stop in a direction along the helical path, the second mechanical stop being spaced a distance away from the first mechanical stop in the direction along the helical path such that a first line drawn through any of the first mechanical stop in a direction transverse to the helical path extends only through the first mechanical stop and a second line drawn through any of the second mechanical stop in the direction transverse to the helical path extends only through the second mechanical stop, the first and second mechanical stops positioned offset from the helical path and configured to come in contact with an opposing surface of the force sensor to prevent overstretching and overbending of the spring.

2. The apparatus according to claim 1, wherein the first and second mechanical stops include opposing sigmoid curves.

3. The apparatus according to claim 1, wherein the first and second mechanical stops are configured to engage simultaneously so that a force applied on the spring is shared among the first and second mechanical stops to prevent sequential failure of the first and second mechanical stops.

4. The apparatus according to claim 3, wherein the at least one helical cut comprises multiple helical cuts, respective ones of the first and second mechanical stops of each of the helical cuts being configured to engage simultaneously.

5. The apparatus according to claim 3, wherein the at least one helical cut comprises multiple helical cuts, the first and second mechanical stops of each of the helical cuts being configured to engage simultaneously.

6. The apparatus according to claim 1, wherein respective ones of the first and second mechanical stops including respective T-shape elements disposed in respective T-shape openings.

7. The apparatus according to claim 1, wherein of the first and second mechanical stops include respective loops and sockets.

8. The apparatus according to claim 1, wherein the at least one helical cut comprises multiple helical cuts, the tube comprising three of the helical cuts.

9. The apparatus according to claim 1, further comprising a proximal coupler having a proximal and distal end, wherein the elongated deflectable element has a distal end connected to the proximal end of the proximal coupler, the tube and the distal end of the proximal coupler including complementary bayonet connecting features connecting the distal end of the proximal coupler with the tube.

10. The apparatus according to claim 1, further comprising a distal coupler, wherein the tube has a distal end comprising holes disposed around the circumference of the tube, the distal end of the tube being connected top the distal coupler via an adhesive which extends into respective ones of the holes.

11. The apparatus according to claim 10, wherein the tube includes a distal edge with openings therein, the distal coupler including protrusions configured for engaging the openings to prevent rotations of the distal coupler with respect to the tube.

12. The apparatus according to claim 11, wherein the openings include U-shaped openings.

13. The apparatus according to claim 1, further comprising a distal coupler, wherein the tube includes a distal edge with openings therein, the distal coupler including protrusions configured for engaging the openings to prevent rotation of the distal coupler with respect to the tube.

14. The apparatus according to claim 13, wherein the openings include U-shaped openings.

15. The apparatus according to claim 1, wherein the distal assembly includes an expandable distal assembly.

16. The apparatus according to claim 15, wherein the expandable distal assembly includes an inflatable balloon.

17. The apparatus according to claim 1, wherein the force sensor includes a transmitting coil and at least one receiving coil disposed on the tube.

18. The apparatus according to claim 1, wherein the first and second mechanical stops are positioned such that the first mechanical stop is oriented symmetrically from the second mechanical stop.

19. The apparatus according to claim 1, wherein the helical path extends at most two-thirds around the circumference of the tube.

* * * * *